United States Patent
Willis

(10) Patent No.: US 11,241,214 B2
(45) Date of Patent: Feb. 8, 2022

(54) METHOD AND APPARATUS FOR ULTRASOUND GUIDED REFILLING OF A DRUG DELIVERY PUMP

(71) Applicant: Clarius Mobile Health Corp., Burnaby (CA)

(72) Inventor: David Glenn Willis, Woodinville, WA (US)

(73) Assignee: Clarius Mobile Health Corp., Vancouver (CA)

( * ) Notice: Subject to any disclaimer, the term of this patent is extended or adjusted under 35 U.S.C. 154(b) by 577 days.

(21) Appl. No.: 16/115,514

(22) Filed: Aug. 28, 2018

(65) Prior Publication Data

US 2020/0069283 A1 Mar. 5, 2020

(51) Int. Cl.
*A61B 8/00* (2006.01)
*A61B 90/00* (2016.01)
(Continued)

(52) U.S. Cl.
CPC ........ *A61B 8/4209* (2013.01); *A61B 17/3403* (2013.01); *A61B 17/3468* (2013.01);
(Continued)

(58) Field of Classification Search
CPC ... A61B 8/4209; A61B 90/39; A61B 17/3403; A61B 17/3468; A61B 2017/3413;
(Continued)

(56) References Cited

U.S. PATENT DOCUMENTS

| 2010/0041990 A1 | 2/2010 | Schlitt et al. | |
| 2011/0092811 A1* | 4/2011 | Yasui | A61B 5/489 600/424 |

(Continued)

OTHER PUBLICATIONS

Weill Cornell Medicine, "Pain Management", Neuromodulation, publication date unknown, available online: https://painmanagement.weillcornell.org/health-library/neuromodulation, last accessed Jun. 20, 2018.

(Continued)

*Primary Examiner* — Yi-Shan Yang
(74) *Attorney, Agent, or Firm* — Julian Ho

(57) ABSTRACT

An apparatus for the ultrasound guided refilling of a drug delivery pump includes an ultrasound imaging transducer having a nosepiece and a support device coupled to the nosepiece of the ultrasound imaging transducer. The support device can have two support holes whose centers are positioned along a horizontal axis of the support device. A marker can be placed in each of the two support holes. The vertical axis of the ultrasound imaging transducer coincides with the vertical axis of the support device. When imaging using this apparatus and the port inlet of the pump is visualized using the ultrasound transducer, two primary marks on skin can be created by inserting a marker into the support holes. The apparatus can then be rotated around its vertical axis, and a marker again inserted into the support holes to create two secondary marks. The inlet port of the pump is then marked at the intersection of lines which connects the primary marks and respectively the secondary marks.

20 Claims, 7 Drawing Sheets

(51) Int. Cl.
*A61B 17/34* (2006.01)
*A61M 31/00* (2006.01)

(52) U.S. Cl.
CPC ........... *A61B 90/39* (2016.02); *A61M 31/002* (2013.01); *A61B 2017/3413* (2013.01); *A61B 2090/3925* (2016.02); *A61B 2090/3983* (2016.02)

(58) Field of Classification Search
CPC .... A61B 2090/3925; A61B 2090/3983; A61B 17/3478; A61B 2090/395; A61B 2017/00924; A61M 31/002; A61M 2205/3375; A61M 2209/045; A61M 5/14276
See application file for complete search history.

(56) References Cited

U.S. PATENT DOCUMENTS

2017/0196591 A1* 7/2017 Long, Jr. ................. A61B 34/20
2019/0282262 A1* 9/2019 Bouazza-Marouf ........................ A61B 17/3403

OTHER PUBLICATIONS

Abstract of Gail L. McGlothlen DNP, RN., Lori Rodriguez PHD RN., Training for the Intraspinal Drug Delivery System Reservoir Refill Procedure Highly Varialbe: A Nationwide Survey of the Healthcare Professionals, Feb. 24, 2017.
Mike Crader, Pump Refill Procedure Safety Update, Medtronic, May 2013.
Michael Gofeld MD., Carlton McQueen MD., Ultrasound-Guided Intrathecal Pump Access and Prevention of Pocket Refill, Apr. 15, 2011,Pain Medicine, vol. 12, Issue 4, pp. 607-611.

* cited by examiner

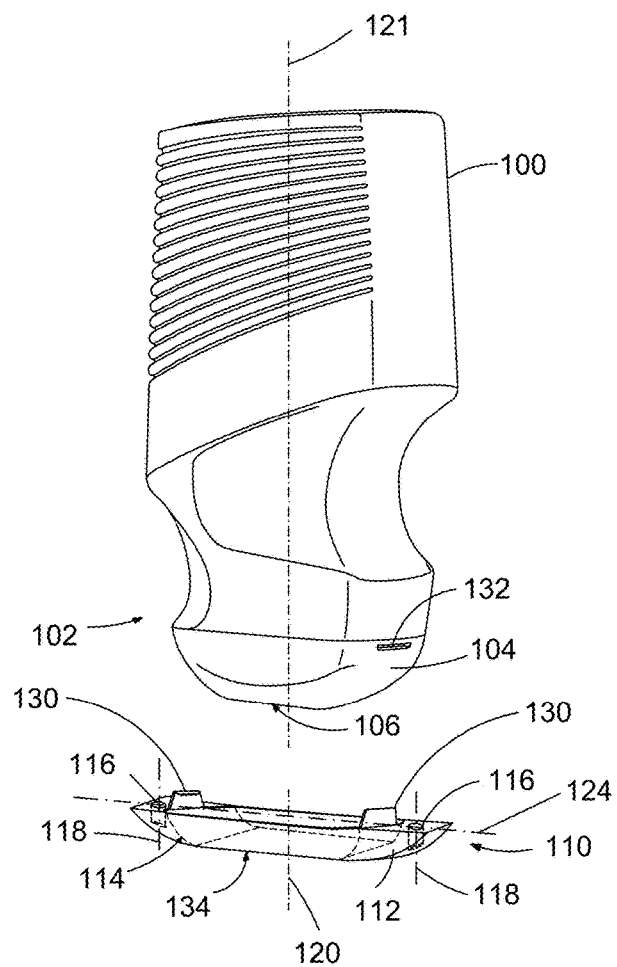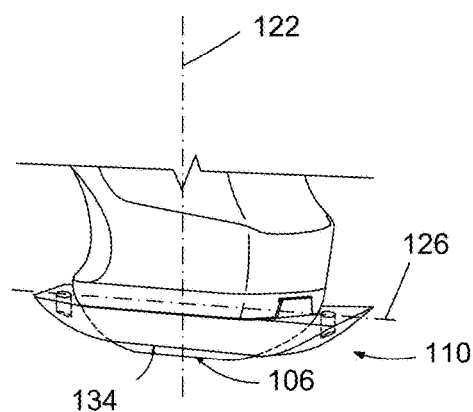
Figure 1A
Figure 1B

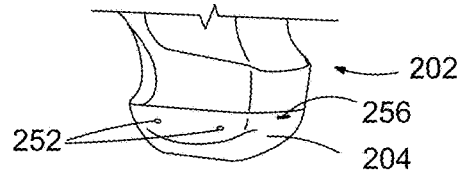
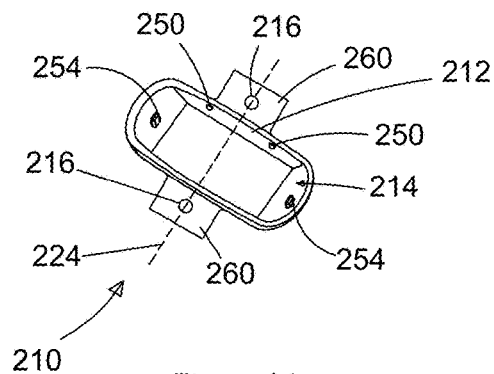
Figure 2A
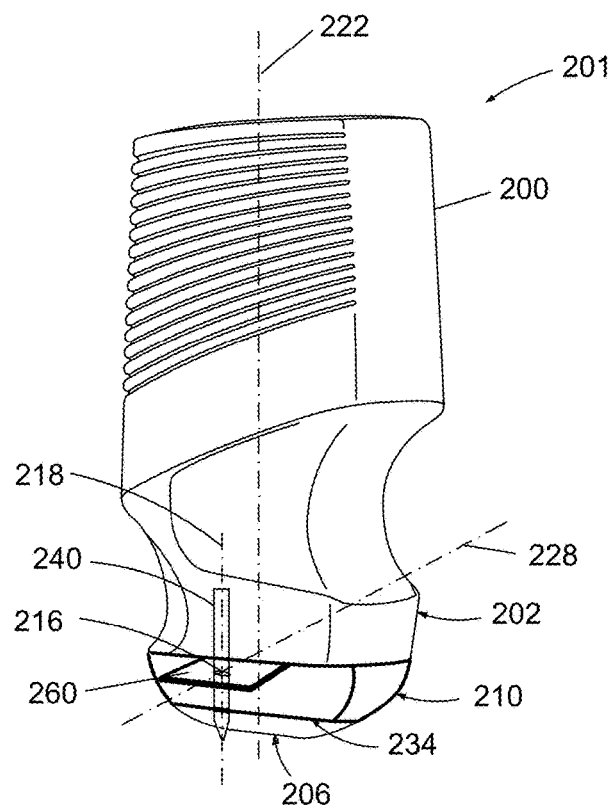
Figure 2B

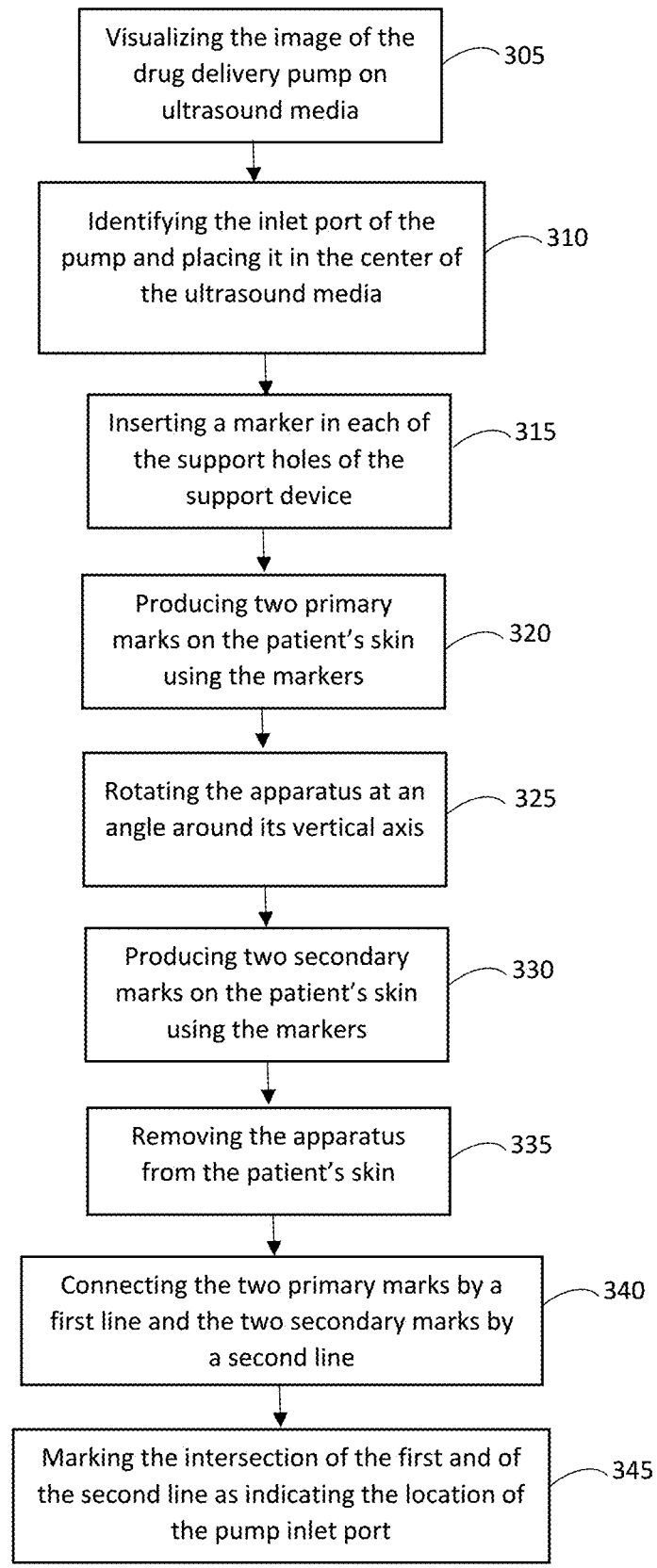

METHOD AND APPARATUS FOR ULTRASOUND GUIDED REFILLING OF A DRUG DELIVERY PUMP

FIELD

The present invention relates to a method and apparatus for ultrasound guided refilling of a drug delivery pump, for example for refilling of a neuromodulation pump.

BACKGROUND

Drug delivery systems which provide long term, periodic delivery of pain medication generally employ a pump, which is placed under the skin during a minor surgical procedure and which needs to be refilled periodically (for example every six months or so). Such implantable pumps used for pain medication, known as neuromodulation pumps, are able to deliver pain medication to a specific target, therefore allowing a lower dosage and decreased side effects.

Neuromodulation pumps are refilled by inserting a needle through the inlet port of the pump. The current practice is to determine the position of the pump by feeling the patient's skin and inserting a needle into the perceived inlet orifice of the pump. Such detection of the pump's inlet port is difficult considering the size of the pump, which is typically about 6 to 8 cm in diameter and about 2 cm in thickness and with a very small inlet orifice of about 1 to 2 cm in diameter. The pump can move around after implantation and this makes their refilling even more difficult. Such a refill procedure requires highly trained professionals to minimize the risk for human error during the pump reservoir refill procedure as affirmed by the International Neuromodulation Society in their publication entitled "Training for the intraspinal drug delivery system reservoir refill procedure highly variable: A nationwide survey of health care professionals" by Gail L. McGlothlen DNP, RN, Lori Rodriguez PhD, RN, published on Feb. 24, 2017.

There have been several attempts to make this procedure more accurate, to minimize the risks of a pocket fill, which may occur if the needle is not inserted correctly into the refill port and the drug is inadvertently inserted into the patient instead of the pump's reservoir. For example, a refill template based on the model pump being refilled has been used as a guide for inserting the needle into the refill port of the pump as described, for example, in the clinician refill reference card issued by Medtronic in their Pump Refill Procedure Safety Update (March 2013).

This method relies on palpating the area of the implanted pump to identify its location and orientation, aligning the refill template with the left or right edge of the pump, depending on the model of the pump that is being refilled, inserting the needle through the patient's skin and subcutaneous tissue, passing the needle through the septum until it hits the metal bottom of the refill port, emptying the pump if necessary and refilling the pump. Such a method still relies on palpation to identify the position of the pump under the patient's subcutaneous tissue and does therefore require highly trained personnel to perform an accurate procedure and avoid error.

An ultrasound-guided pump access and refill using imaging for both the needle guidance and verification of the injection site has been described in the paper entitled "Ultrasound-Guided Intratechal Pump Access and Prevention of the Pocket Fill" by Michael Gofeld and Carlton K. McQueen (Pain Medication, Volume 12, Issue 4, 1 Apr. 2011, pages 607-611). In this method the injection port of the pump was identified as a hypoechoic rectangle structure by ultrasound imaging using a linear transducer, the injection port was centered on the display screen and the needle insertion was performed in an out-of-plane guidance technique starting immediately cephalad to the midpoint of the transducer. The first attempts using this technique were unsuccessful with the needle tip contacting the pump surface but not the port. This was related to the trajectory of the needle. When the transducer was placed exactly over the port it resulted in a faulty needle placement. The technique was therefore modified such that after port visualization the transducer was tilted about 45 degrees still keeping the port image in the center of the screen and the needle was advanced at the right to the transducer and was inserted into the pump port.

Such a technique of introducing the needle at an angle does not always work because the orifice of the pump is often very superficial, and the needle needs to be inserted vertically.

In view of the known difficulties associated with an accurate refill of the drug delivery pumps there is a need for an apparatus and a method capable of minimizing the risks associated with the existing refill procedure for such pumps. The embodiments discussed herein may address and/or ameliorate at least some of the aforementioned drawbacks identified above. The foregoing examples of the related art and limitations related thereto are intended to be illustrative and not exclusive. Other limitations of the related art will become apparent to those of skill in the art upon a reading of the specification and a study of the drawings herein. Although specific advantages have been discussed herein, various embodiments may include some, none, or all of the enumerated advantages.

It should be understood at the outset that, although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described below.

BRIEF DESCRIPTION OF THE DRAWINGS

The drawings illustrate specific embodiments of the invention, but should not be considered as restricting the spirit or scope of the invention in any way. Unless otherwise specifically noted, articles depicted in the drawings are not necessarily drawn to scale.

FIG. 1A illustrates a linear ultrasound imaging transducer and a support device for marking the location of the inlet port of a drug delivery pump, according to at least one embodiment of the present invention.

FIG. 1B illustrates the support device mounted over the nosepiece of the linear ultrasound transducer illustrated in FIG. 1A, according to at least one embodiment of the present invention.

FIG. 2A illustrates the nosepiece of a linear ultrasound imaging transducer and a support device for marking the location of the inlet port of a drug delivery pump, according to at least another embodiment of the present invention.

FIG. 2B illustrates an apparatus for the ultrasound guided refilling of a drug delivery pump having a linear probe with the support device illustrated in FIG. 2A mounted thereon and with a marker placed in a support hole of the support device, according to at least another embodiment of the present invention.

FIG. 3 illustrates the steps of the method for marking the pump inlet port of a drug delivery pump, according to at least one embodiment of the present invention.

DETAILED DESCRIPTION

Figure 1C:
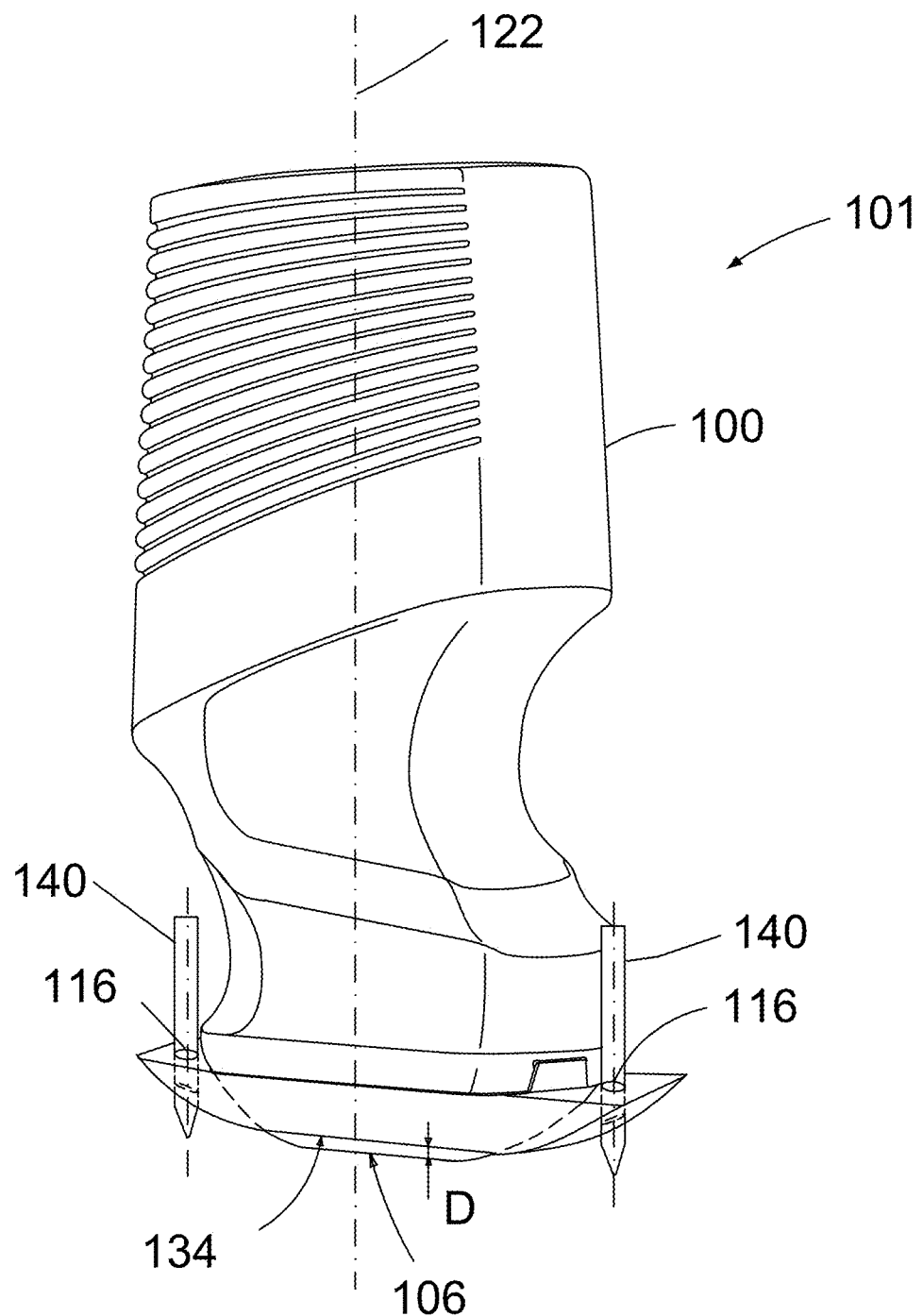
FIG. 1C illustrates an apparatus for the ultrasound guided refilling of a drug delivery pump having the arrangement illustrated in FIG. 1B with markers positioned in the support holes of the support device, according to at least one embodiment of the present invention.

In a first broad aspect of the present disclosure, there is provided an apparatus for ultrasound guided refilling of a drug delivery pump including: an ultrasound imaging transducer having a nosepiece, and a support device coupled to the nosepiece of the ultrasound imaging transducer. The support device includes: a body having a proximal surface engaging the nosepiece of the ultrasound imaging transducer, and at least two support holes which penetrate through the body of the support device and whose centers are positioned along a horizontal axis of the support device, wherein each of the at least two support holes are for insertion of a marker; wherein the vertical axis of the ultrasound imaging transducer coincides with the vertical axis of the support device.

In some embodiments, the horizontal axis of the support device where the centers of the at least two support holes are placed coincides with the short axis of the nosepiece of the ultrasound imaging transducer.

In some embodiments, the horizontal axis of the support device where the at least two support holes are placed coincides with the long axis of the nosepiece of the ultrasound imaging transducer.

In some embodiments, the ultrasound imaging transducer includes a transducer array, and the centers of the support holes coincide with a center portion of the transducer array.

In some embodiments, the support device includes at least one clip in proximity of the proximal surface of the support device, and the nosepiece of the ultrasound imaging transducer has a corresponding at least one slot for receiving the at least one clip when the support device is installed on the ultrasound imaging transducer.

In some embodiments, the support device includes at least one of a protrusion or divot on its proximal surface, and the nosepiece of the ultrasound imaging transducer includes a corresponding at least one of a divot or protrusion for mating to the at least one of the protrusion or the divot on the proximal surface when the support device is installed on the ultrasound imaging transducer.

In some embodiments, the proximal surface of the support device matches the shape of the nosepiece of the ultrasound imaging transducer such that the support device is fitted to the ultrasound imaging transducer during assembly and the support device remains fitted to the ultrasound imaging transducer during operation due to friction.

In some embodiments, the ultrasound imaging transducer includes a transducer array accessible on the nosepiece, and the support device mates with the nosepiece outside of an area of the nosepiece where the transducer array is accessible.

In some embodiments, the vertical axis of the at least two support holes is parallel to the vertical axis of the ultrasound imaging transducer such that when the marker is inserted, the marker is positioned parallel to the vertical axis of the ultrasound imaging transducer.

In some embodiments, the axis of the at least two support holes is inclined relative to the vertical axis of the ultrasound imaging transducer such that when the marker is inserted, the marker is positioned at an angle from the vertical axis of the ultrasound imaging transducer.

In some embodiments, the marker can make a visible marking on a surface covered by ultrasound gel.

In some embodiments, the ultrasound imaging transducer includes a linear scanner.

In some embodiments, the support device includes additional support holes placed along another horizontal axis of the support device, wherein each of the additional holes are for insertion of the marker.

In another broad aspect of the present disclosure, there is provided a method of marking a position of the inlet port of a drug delivery pump on skin, the method including: visualizing the inlet port of the drug delivery pump by using the ultrasound imaging transducer of an apparatus described herein; inserting a marker into each of the at least two support holes to produce at least two primary marks on the skin; rotating the apparatus at an angle around the vertical axis of the ultrasound imaging transducer while maintaining the apparatus over the inlet port of the drug delivery pump; inserting the marker into each of the at least two support holes to produce at least two secondary marks on the skin; drawing a first line to connect the at least two primary marks on the skin; drawing a second line to connect the at least two secondary marks on the skin; and marking the intersection of the first line with the second line as indicating the location of the inlet port of the drug delivery pump.

In some embodiments, the apparatus is rotated at an angle of 90 degrees around the vertical axis of the ultrasound imaging transducer while maintaining the apparatus over the inlet port of the drug delivery pump.

In some embodiments, the method further includes inserting a needle into the skin at the intersection that indicates the location of the inlet port of the drug delivery pump, and refilling the drug delivery pump with medication.

In another broad aspect of the present disclosure, there is provided a method of marking a position of the inlet port of a drug delivery pump on skin, the method including: visualizing the inlet port of the drug delivery pump by using the ultrasound imaging transducer of the apparatus described herein; inserting a marker into each of the at least two support holes and each of the additional support holes, to produce at least four markings on the skin; drawing a first line to connect the two opposite markings on the skin; drawing a second line between the other two opposite markings on the skin; and marking the intersection of the first line with the second line as indicating the location of the inlet port of the drug delivery pump.

In another broad aspect of the present disclosure, there is provided a support device for coupling to a nosepiece of an ultrasound imaging transducer, the support device including a body having a proximal surface configured to engage the nosepiece of the ultrasound imaging transducer, and at least two support holes which penetrate through the body of the support device and whose centers are positioned along a horizontal axis of the support device.

In some embodiments, the at least two support holes are placed along an axis that corresponds to a short axis of the nosepiece of the ultrasound imaging transducer.

In some embodiments, the at least two support holes are placed along an axis that corresponds to the long axis of the nosepiece of the ultrasound imaging transducer.

In some embodiments, the support device further includes at least one clip in proximity to the proximal surface of the support device, the at least one clip for coupling to the nosepiece of the ultrasound imaging transducer.

In some embodiments, the support device further includes at least one of a protrusion or a divot on its proximal surface, the at least one of a protrusion or a divot for coupling to the nosepiece of the ultrasound imaging transducer.

In some embodiments, the proximal surface of the support device matches a shape of the nosepiece of the ultrasound imaging transducer such that when the support device is fitted to the ultrasound imaging transducer during assembly it remains fitted thereto due to friction.

In some embodiments, the ultrasound imaging transducer includes a transducer array, and the centers of the support holes coincide with a center portion of the transducer array.

For simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, certain steps, signals, protocols, software, hardware, networking infrastructure, circuits, structures, techniques, well-known methods, procedures and components have not been described or shown in detail in order not to obscure the embodiments generally described herein.

Furthermore, this description is not to be considered as limiting the scope of the embodiments described herein in any way. It should be understood that the detailed description, while indicating specific embodiments, are given by way of illustration only, since various changes and modifications within the scope of the disclosure will become apparent to those skilled in the art from this detailed description. Accordingly, the specification and drawings are to be regarded in an illustrative, rather than a restrictive, sense.

Referring to FIG. 1A, shown there generally as 100 is an example ultrasound imaging transducer which may be provided in the form of a handheld wireless scanner that may be configured to communicate with an external wireless computing device (e.g., a tablet computer) containing a display (not shown). In various embodiments, the ultrasound imaging transducer may be provided in the form of an ultrasound probe that can be attached via a cord to a smart device (e.g., a smartphone or tablet computer) or a separate ultrasound machine.

A support device 110 may be attached to the transducer's head 102 which includes a nosepiece 104 holding a transducer array on its surface 106. The surface 106 of the nosepiece 104 which carries the transducer array may come into contact with the patient's skin when a medical investigation is performed as part of a method of the present invention.

The support device 110 has a body 112 having: a proximal surface 114, which may be configured to mate with the transducer head 102 of the ultrasound imaging transducer 100; and two support holes 116, which penetrate through the body 112 of the support device 110. In the illustrated embodiment, the axis 118 of each of the two support holes 116 may be parallel to the vertical axis 120 of the support device 110. Additionally or alternatively, this axis 118 can be inclined relative to the vertical axis 120 of the support device 110. Generally, the vertical axis 120 of the support device 110 aligns with the vertical axis 121 of transducer 100 forming a common axis 122 when they are mounted together as illustrated in FIG. 1B. The centers of the two support holes 116 may be positioned along a horizontal axis 124 of the support device 110. In the embodiment illustrated in FIGS. 1A, 1B and 1C, when the support device 110 is mounted on the transducer 100, the horizontal axis 124 of the support device 110 coincides with the long axis 126 of the transducer 100 (as shown in FIG. 1B).

In the illustrated example embodiment of FIG. 1A, the support device 110 includes two clips 130 positioned in the proximity of the proximal surface 114 of the support device 110. The nosepiece 104 has corresponding slots 132 (only one being shown in FIG. 1A), such that when the support device 110 is mounted on the nosepiece 104 of the transducer 100, each slot 132 receives one clip 130 to thereby secure the fixed position of the support device 110 relative to the transducer 100. For example, the clips 130 may slide over the body of the nosepiece 104 to engage the slots 132 when the support device 110 is mounted on the transducer 100, and the support device 110 can be removed from this assembly by physically pulling on the support device 110 such that the clips 130 disengage from the slots 132.

Other methods for attaching the support device 110 on the nosepiece 104 of the transducer 100 may be possible. For example, a slidable latch may be provided in some embodiments. Additionally or alternatively, the proximal surface 114 can be configured to mate with the transducer head 102 via a friction fit. A further way for attaching the support device 110 on the nosepiece 104 of the transducer 100 can be possible, as shown and described in the embodiment illustrated in FIGS. 2A and 2B.

Referring to FIG. 1C, when the support device 110 is fixed in its position on the transducer head 102, the distal surface 134 of the support device 110 may lie by a distance "D" above the surface 106 of the nosepiece 104 that makes the transducer array accessible, such that the area of the transducer array is not covered and the ultrasound rays emitted by the transducer 100 during operation are not obstructed and can reach the skin of the patient.

In some embodiments, where the support device 110 is made of an acoustically-transparent material that allows for transmission ultrasound energy, the distal surface 134 of the support device could partially or totally cover the surface 106.

Referring still to FIG. 1C, the apparatus 101 for ultrasound guided refilling of a drug delivery pump according to the present invention is shown with a marker 140 inserted into each of the two support holes 116. While illustrated with different markers 140 inserted simultaneously into each of the support holes 116, in various embodiments, the same (one) marker 140 can be inserted into the two support holes 116 sequentially. Because in this embodiment the vertical axis 118 of each of the holes 116 (as shown in FIG. 1A) is parallel to the common axis 122 of the transducer 100 and of the support device 110 (as illustrated in FIG. 1C), the two markers 140 have a vertical position when inserted in holes 116 and will contact the skin of the patient perpendicularly during the marking process. In some other embodiments, the vertical axis of each of the holes 116 may be inclined relative to the common axis 122 and the markers 140 will contact the patient's skin from an inclined position during the marking process. For example, this may allow the marks made by the markers 140 to be made closer to transducer array, and reduce the distance between the marks. In turn, this may make it easier to draw the line connecting the marks created by insertion of the markers 140 into the support holes 116 (as discussed below).

In the embodiment of FIGS. 1A-1C, the horizontal axis 124 of the support device 110 where the two support holes 116 are placed coincides with the long axis 126 of the nosepiece 104 of the ultrasound imaging transducer 100.

In some embodiments, the markers 140 used in the present embodiments may include an ink that is capable of making a visible mark on a surface covered by ultrasound gel. For example, this may be desirable because the ultrasound gel used when visualizing the inlet port may potentially bleed out beyond the immediate contact surface 106 of the transducer 100, so as to be on an area of the skin where the marker 140 is to make its mark.

As discussed above, the vertical axis of the support holes 116 may be configured to be inclined relative to the common axis 122 (e.g., so that the marking end of markers 140 inserted into the holes 116 are closer to the transducer array at the contact surface 106). While this may make it easier to draw the line connecting the marks, such a configuration may potentially put the head of the marker 140 closer to any ultrasound gel. If a marker 140 is used that cannot make good markings on skin covered by ultrasound gel, such a configuration may make it difficult to get clear markings on the skin. Thus, in some embodiments, the vertical axis of the support holes 116 may be configured to be angled away from the contact surface 106 of the transducer 100.

In various embodiments, the marker 140 may not need to contain any ink at all. For example, the marker 140 may simply be a tool that is sufficient to make an indentation on the skin that can be sufficiently visible to allow for drawing of the lines connecting the marks created by the markers 140 (as discussed below).

In some embodiments, the ultrasound imaging transducer 100 is a linear scanner, as illustrated herein. Due to the higher resolution in near field imaging that is possible, a linear scanner may allow for a more precise identification of the pump (which is typically positioned at a relatively shallow position beneath the skin). However, in other embodiments, a curvilinear imaging scanner can also be used.

In some embodiments, not illustrated herein, the support device 110 can include two additional holes placed along on another horizontal axis of the support device 110. These holes may be similar in shape to the support holes 116. In use, after the inlet port of the drug delivery pump has been identified during ultrasound imaging, a marker 140 may be inserted successively into each of the four holes.

Another embodiment of the present invention is illustrated in FIGS. 2A and 2B. This embodiment is similar to the first embodiment described above and includes a support device 210 which may be coupled to the nosepiece 204 of the transducer head 202 of an ultrasound imaging transducer 200. The support device 210 has a body 212 having a proximal surface 214 which may be configured to mate with the nosepiece 204 of the transducer 200. In this embodiment, the proximal surface 214 may be provided, on opposite sides, with protrusions 250 (only one side is illustrated) and the nosepiece 204 may be provided with divots 252 so that a snap fit can be formed between support device 210 and nosepiece 204 when the support device 210 is mounted on the transducer head 202. Any suitable shape can be used for the protrusions and the matching divots.

As illustrated, in this embodiment, the divots are provided on the nosepiece 204 and the corresponding protrusions are provided on the support device 210. In other embodiments, however, the divots can be provided on the support device 210 and the matching protrusions can be provided on the nosepiece 204 of the transducer 200. In the illustrated embodiment, the support device 210 is further provided with one or more locator posts 254 designed to be positioned against one or more locator slots 256 on the nosepiece 204. Such locator posts 254 are configured to maintain a predetermined desired positioning of the support device 210 with respect to the nosepiece 204 and to prevent the support device 210 from being pushed too far over the nosepiece 204.

In the embodiment shown in FIGS. 2A and 2B, the body 212 of the support device 210 includes two extensions 260 which each carry a support hole 216 for supporting a marker 240 as illustrated in FIG. 2B. The centers of support holes 216 are positioned along a horizontal axis 224 of the support device 210. When the support device 210 is mounted on the transducer head 204, this horizontal axis 224 coincides with the short axis 228 of the transducer 200 as illustrated in FIG. 2B. Whereas the support holes 116 in the embodiment of FIGS. 1A-1C were positioned along a long horizontal axis of the support device, the support holes 216 in the embodiment of FIGS. 2A-2B are positioned along the short horizontal axis of the support device 210.

The ultrasound imaging transducer 200 may provide a transducer array on its surface 206. In the illustrated embodiments, the centers of the support holes 216 may coincide with a center portion of the transducer array. This may facilitate alignment of the mark being made with the marker 240 with the inlet port of the drug pump when the inlet port is visually centered on ultrasound media (as discussed below).

Referring still to FIGS. 2A-2B, when the support device 210 is fixed in its position on the transducer's head 202, the distal surface 234 of the support device 210 lies above the contact surface 206 of the nosepiece 204 such that the area of the transducer array which is provided on this surface 206 is not covered. This allows the ultrasound rays emitted by the transducer 200 during operation to not be obstructed, so that they can reach the skin of the patient. In other embodiments, as discussed before, the support device 210 can be made of an acoustically-transparent material and the distal surface 234 of the support device 210 could partially or totally cover the contact surface 206.

In FIG. 2B, the apparatus 201 for ultrasound guided refilling of a drug delivery pump includes the ultrasound imaging transducer 200, the support device 210 mounted on the transducer head 202 and a marker 240 placed in one of the support holes 216 provided on the support device 210. As in the first embodiment discussed above, the vertical axis of the holes 216 coincides with the vertical axis 218 of the markers 240. Also, as illustrated, this axis 218 is parallel to the vertical axis of the transducer 200, which is the common axis 222 of the transducer 200 and of the support device 210 as illustrated in FIG. 2B. As illustrated, the marker 240 has a vertical position when mounted in holes 216 and will contact the skin of the patient perpendicularly during the marking process. However, in some other embodiments (as discussed above with respect to the embodiments of FIGS. 1A-1C), the vertical axis of the holes 216 can be inclined relative to the common axis 222 and the markers have an inclined position relative to the patient's skin during the marking process.

In this second embodiment, the horizontal axis 224 of the support device 210 (as shown in FIG. 2A) where the two support holes are positioned coincides with the short axis 228 of the nosepiece 204 of the ultrasound imaging transducer 200.

In various embodiments, the holes 116, 216 described herein may generally be of various depths. For example, the hole 116 shown in the embodiment of FIG. 1A is illustrated as having a greater depth than the hole 216 in FIG. 2B. In various embodiments, the depths of the holes 116, 216 can be configured to be of a sufficient depth to accurately guide the marker 140 to the skin without allowing the head of the marker 140 to pivot. Such a configuration may reduce the possibility of the mark being slightly offline the center of the horizontal axis of the holes 116, 216.

The process of marking the inlet port of the pump will now be described in connection with FIGS. 3, 4, 5A-5B and 6A-6B. In discussing these figures, reference will simultaneously be made to the various components discussed above in relation to FIGS. 1A-1C, and 2A-2B. While the methods discussed below is made with reference to the components of the two different embodiments of FIGS. 1A-1C and 2A-2B, it will be understood that the method may be practised on each one of these embodiments individually and independently, without reference to the other embodiment.

Referring to FIG. 3, at 305, a first act of the marking process may involve visualizing the image of the drug delivery pump on ultrasound media displayed on a screen. This can be performed by moving the ultrasound imaging transducer 100, 200 of the marking apparatus 101, 201 on the patient's skin until the inlet port of the pump is identified.

Figure 4:
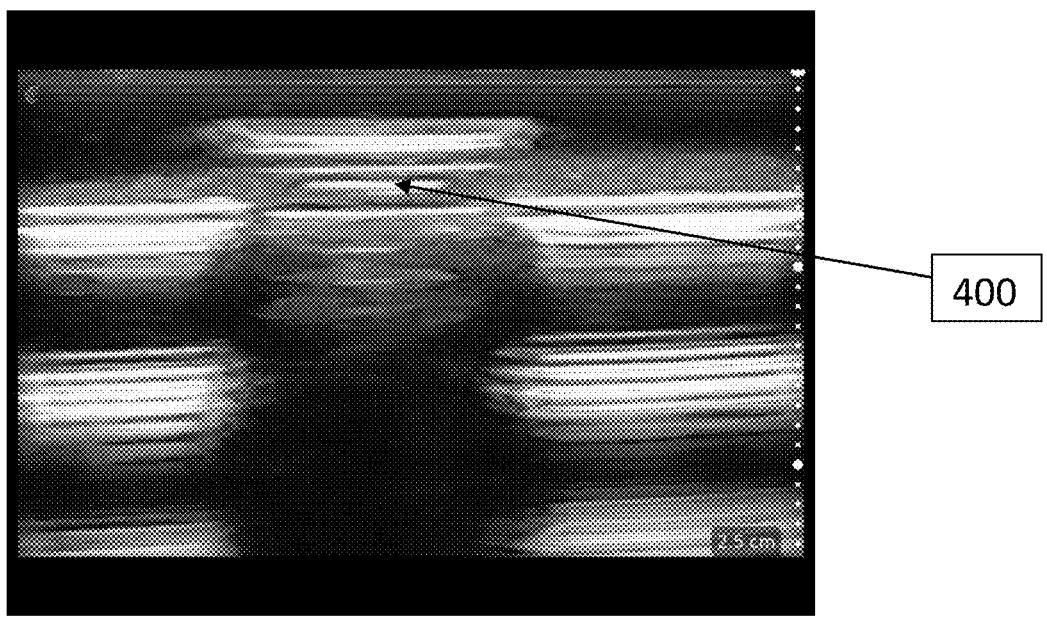
FIG. 4 illustrates an ultrasound image used to identify the inlet port of the drug delivery pump, according to at least one embodiment of the present invention.

At 310, the method may involve identifying the inlet port of the pump and placing it in the center of the ultrasound media. An example of such an image is shown in FIG. 4. For example, the inlet port of the drug delivery pump may appear as indicated by reference number 400 in FIG. 4. Once the pump inlet port is visualized and identified in the center of the ultrasound media, at 315, a marker 140, 240 may be inserted into each of the two support holes 116, 216 of the support device 110, 210. The insertion of the marker(s) 140, 240 may produce two primary marks on the skin of the patient (act 320).

The next act may be to rotate the apparatus 101, 201 at an angle around the vertical common axis 122, 222 (act 325). The same marker(s) 140, 240 may then be used to produce two secondary marks on the patient's skin (act 330). In some embodiments, the marking apparatus 101, 201 may be rotated 90 degrees prior to creation of the secondary marks, but any rotation degree may be acceptable as long as the vertical axis of the transducer 100, 200 which is the common axis 122, 222 of the apparatus 101, 201 is maintained over the identified inlet port of the pump.

At 335, the medical personnel may remove the marking apparatus 101, 201 from contacting the patient's skin. At 340, a line can be drawn on the patient's skin by connecting the two primary marks and a second line can be drawn between the two secondary marks. At 345, the medical personnel may then mark the intersection of the first line with the second line to obtain a marking which indicates the location of the inlet port of the drug delivery pump.

Figure 5A:
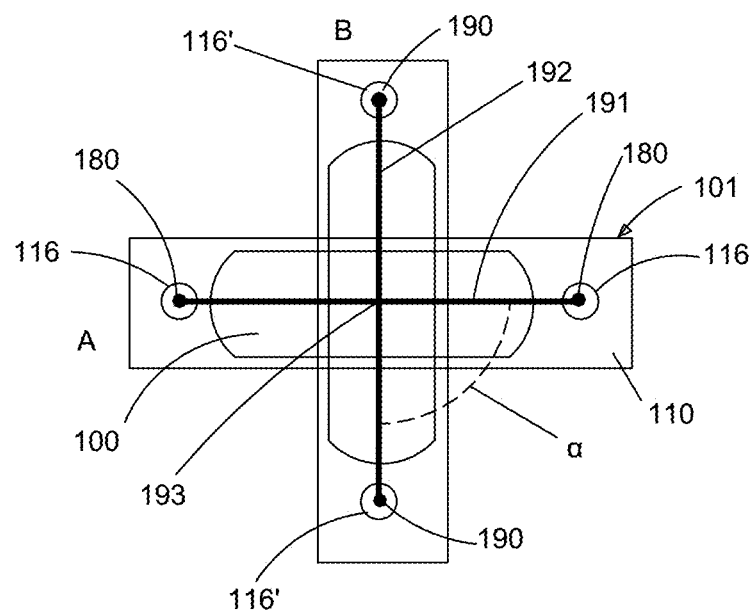
FIGS. 5A and 5B illustrate the markings produced using the apparatus of FIG. 1C to mark the inlet port of the drug delivery pump on the skin of a patient, according to at least two embodiments of the present invention.
Figure 5B:
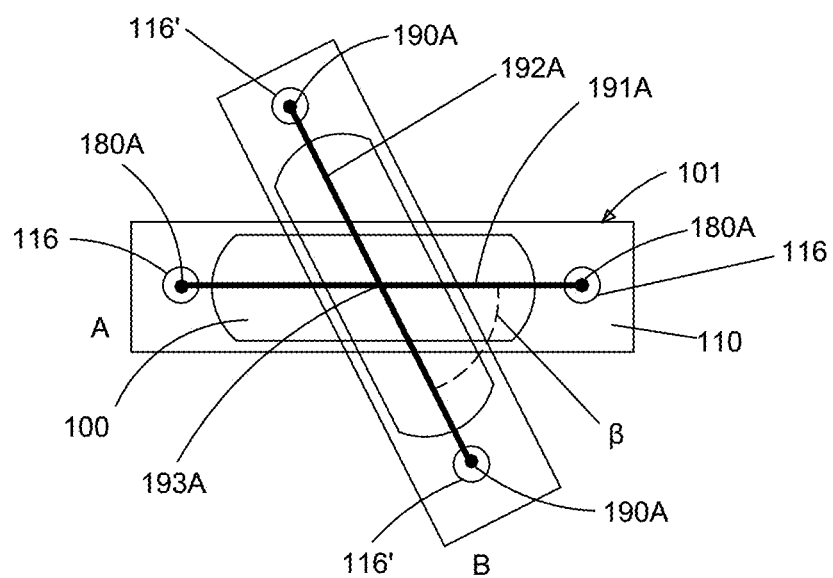

Referring to FIGS. 5A and 5B, shown there are schematic drawings illustrating the markings produced when performing the methods described herein with the apparatus of the first embodiment of FIG. 1C. The apparatus 101 may be placed over the patient's body in position such that the inlet port of the drug delivery pump may be visualized in the center of the ultrasound media using the ultrasound imaging transducer 100. The apparatus 101 can be maintained in position 'A' and the marker 140 may be placed in the support holes 116 of the support device 110 to produce two primary marks 180 on the patient's skin. Then, the apparatus 101 can be rotated clockwise by a 90 degree angle 'α', for example, as illustrated in FIG. 5A to reach a position 'B' and the marker 140 may be placed in the support holes 116' of the support device 110 to produce two secondary marks 190. The apparatus 101 may then be removed from the patient's skin.

The two primary marks 180 may be connected by using a marker 140 to draw a first line 191 on the patient's skin. The two secondary marks 190 may then be connected by using a marker 140 to draw a second line 192 on the patient's skin. The intersection 193 of the first line 191 and of the second line 192 may then be marked as indicating the location of the pump inlet port.

FIG. 5B shows a variation of the method illustrated in FIG. 5A whereby the primary marks 180A are first obtained when a marker 140 is placed in the support holes 116 of the apparatus 101 with ultrasound imaging transducer 100, and the apparatus 101 is maintained in position 'A'. Then, the secondary marks 190A are obtained after the apparatus 101 is rotated by an angle 'β' to reach position 'B', and the marker 140 may again be inserted into support holes 116'. In this case, the rotation angle β may be smaller than 90 degrees. Primary markers 180A are then connected by drawing a first line 191A and secondary marks 190A are connected by drawing a second line 192A. The intersection 193A of the first line 191A and the second line 192A can then be marked as indicating the location of the inlet port of the pump.

Figure 6A:
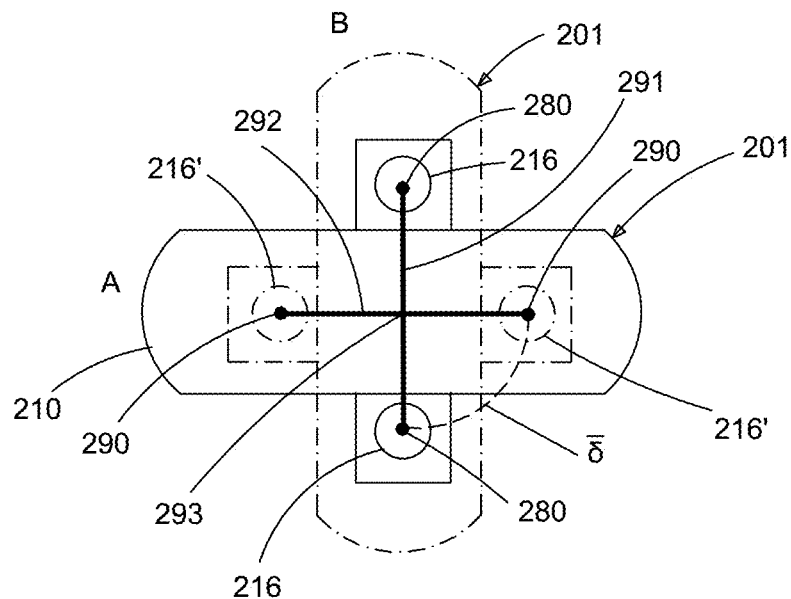
FIGS. 6A and 6B illustrate the markings produced using the apparatus of FIG. 2B to mark the inlet port of the drug delivery pump, according to at least two embodiments of the present invention.
Figure 6B:
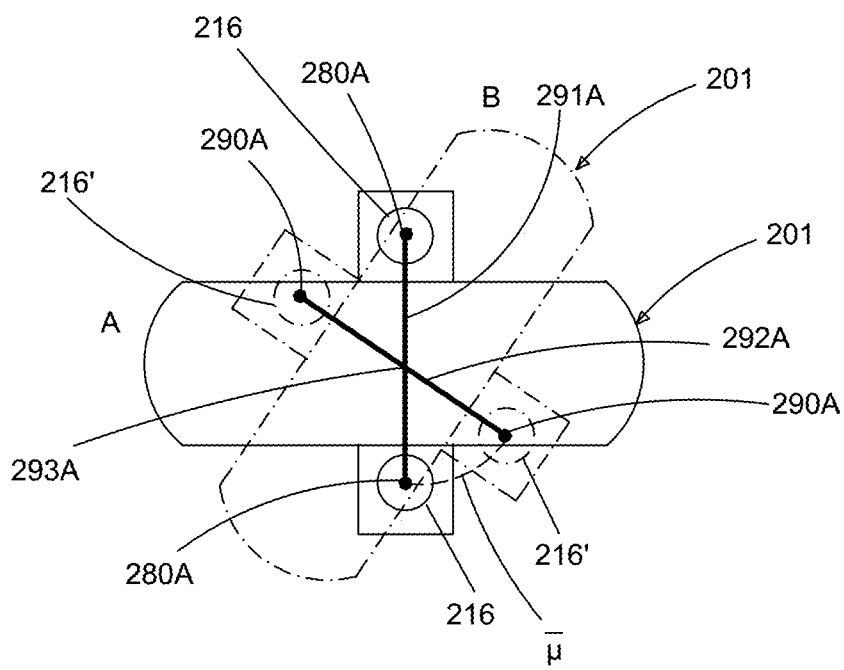

FIGS. 6A and 6B illustrate the markings produced with the second embodiment of the present disclosure illustrated in FIGS. 2A and 2B above. The apparatus 201 may be placed over the patient's body in position 'A' such that the inlet port of the drug delivery pump may be visualized in the center of the ultrasound media and a marker 240 may be inserted into the support holes 216 of the support device 210 and are used to produce two primary marks 280 on the patient's skin.

Then the apparatus 210 may be rotated by a 90 degree angle 'δ' clockwise, for example, as illustrated in FIG. 6A to reach a position 'B' and then the marker 240 may be placed in the support holes 216' of the support device 210 to produce two secondary marks 290. The apparatus 201 may then be removed from the patient's skin. The two primary marks 280 are connected by using a marker 240 to draw a first line 291 on the patient's skin, the two secondary marks 290 are connected by using a marker 240 to draw a second line 292 on the patient's skin. The intersection 293 of the first line 291 with the second line 292 may then be marked as indicating the location of the pump inlet port.

FIG. 6B illustrates a method similar to the one illustrated in FIG. 5B whereby the primary marks 280A are first obtained when a marker 240 is inserted into support holes 216 when the apparatus 201 is maintained in position 'A'. Then, the secondary marks 290A are obtained after the apparatus 201 is rotated by an angle 'μ' (smaller than 90 degrees, and as illustrated, in a counter clockwise direction) to reach position 'B', and the marker 240 may be inserted into support holes 216'. Primary marks 280A are then connected by drawing a first line 291A and secondary marks 290A are connected by drawing a second line 292A. The intersection 293A of the first line 291A and the second line 292A can then marked as indicating the location of the inlet port of the pump.

FIGS. 5B and 6B demonstrate that the rotation angle of the apparatus 101, 201 for the ultrasound guided refilling of a drug delivery pump does not have to be 90 degrees; and it can be any angle as long as the vertical axis of the ultrasound transducer 100, 200 is maintained over the inlet port of the pump as visualized on the ultrasound imaging screen.

In the embodiments described above, the ultrasound imaging transducer 100, 200 is illustrated as a linear scanner. However, in various embodiments, a curvilinear or other suitable type of transducer may be used.

In the embodiments illustrated herein, the support device 110, 210 of the present disclosure may be provided with two holes, each hole being able to support a marker 140, 240. In other embodiments, the support device 110, 210 could be provided with two additional holes placed along another horizontal axis of the support device 110, 220, and the additional holes could also be used to support a marker 140, 240 such that once the apparatus 101, 201 is positioned with the vertical axis of the ultrasound imaging transducer 100, 200 over the inlet port of the pump, a marker 140, 240 can be placed in the four support holes and four marks can then be produced without having to rotate the apparatus 101, 201. Opposing marks can then be connected with lines in a manner similar to discussed above. This may produce a final mark indicating the position of the inlet port of the pump at the intersection of the two lines, as described above.

In the embodiments illustrated in the present figures, the proximal surface 114, 214 of the support device 110, 210 generally matches the shape of the nosepiece 104, 204 of the ultrasound imaging transducer 100, 200 such that the support device 110, 210 can be fitted to the ultrasound imaging transducer 100, 200 during assembly and it remains fitted to the ultrasound imaging transducer 100, 200 during operation due to friction. In some other embodiments, the proximal surface 114, 214 of the support device 110, 210 does not match the size and/or shape of the nosepiece 104, 204 and there could be some free space left between the nosepiece 104, 204 and the support device 110, 210.

As discussed above, the support device 110, 210 was generally coupled to an ultrasound transducer 100, 200 having a nosepiece 104, 204. However, in some embodiments, the support device 110, 210 may be attached to the body of the transducer 100, 200 itself. Further, any method of attaching a support device 110, 210 to a transducer 100, 200 is within the contemplation of the present embodiments, regardless of whether the construction of an ultrasound transducer includes a nosepiece or otherwise.

In some embodiments, the support holes discussed herein may not be provided on a support device at all. For example, the support holes may be constructed to form part of the transducer itself (e.g., formed on the nosepiece itself and/or onto the body of the transducer). For example, this may be suitable if the ultrasound transducer is a transducer specifically designated for use in refilling drug pumps, as discussed herein.

The present embodiments may be desirable in that the inlet port of a drug delivery pump may be easily and precisely identified without having to use an invasive method and with minimal discomfort to the patient. For example, while it may be possible to mark a patient's skin without the support device of the present embodiments, many clinicians performing refill of the drug delivery pump are new at using ultrasound technology such that they may find it difficult to hold the ultrasound transducer with one hand while marking the skin with the other. They may also have trouble placing the marker while maintaining the inlet port visually centered on the ultrasound screen.

The support device may reduce challenges associated with placement of the marker by providing support holes corresponding to the correct location for marker placement relative to the position of the transducer on a patient's skin. Thus, the clinician may not need to look at both the ultrasound screen to keep the visualized inlet port centered thereon, and also the ultrasound transducer positioned on the patient's skin when marking the patient's skin.

Since the support holes are already configured at the correct location for marker placement, the clinician may focus on centering the visualized inlet port on the ultrasound screen and, without diverting their visual gaze from the ultrasound screen, use the support holes to guide the pen to mark the correct location by touch. This may be particularly desirable in the embodiments described above with respect to FIGS. 2A-2B and 6A-6B where it may be particularly difficult to correctly place the marker in a position that corresponds to the center position of the transducer array without looking away from the ultrasound screen.

While a number of exemplary aspects and embodiments have been discussed above, those of skill in the art will recognize that may be certain variations, modifications, permutations, additions and sub-combinations thereof. While the above description contains many details of example embodiments, these should not be construed as essential limitations on the scope of any embodiment. Many other ramifications and variations are possible within the teachings of the various embodiments.

Interpretation of Terms

Unless the context clearly requires otherwise, throughout the description and the claims:

"comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

the singular forms "a", "an", and "the" also include the meaning of any appropriate plural forms.

Unless the context clearly requires otherwise, throughout the description and the claims:

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, and/or combinations of two or more of these.

While processes or blocks are presented in a given order herein, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

Where a component (e.g. a device, apparatus, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure that performs the function in the illustrated exemplary embodiments of the invention.

To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments. In some embodiments, the components of the systems and apparatuses may be integrated or separated. Moreover, the operations of the systems and apparatuses disclosed herein may be performed by more, fewer, or other components and the methods described may include more, fewer, or other steps.

It is therefore intended that the following appended claims and claims hereafter introduced are interpreted to include all such variations, modifications, permutations, additions, omissions, and sub-combinations as may reasonably be inferred. The scope of the claims should not be limited by the embodiments set forth in the examples, but should be given the broadest interpretation consistent with the description as a whole.

I claim:

1. An apparatus for ultrasound guided refilling of a drug delivery pump by marking a location for needle insertion, comprising:
   an ultrasound imaging transducer having a nosepiece, and
   a support device coupled to the nosepiece of the ultrasound imaging transducer, the support device comprising:
      a body having a proximal surface engaging the nosepiece of the ultrasound imaging transducer, and
      at least two support holes which penetrate through the body of the support device,
      where the centers of the at least two support holes are positioned along a horizontal axis of the support device,
      wherein a vertical axis of the ultrasound imaging transducer coincides with a vertical axis of the support device, forming a common vertical axis,
      wherein the at least two support holes are positioned to secure the removable insertion of a marker, to create first points that form a first line,
      wherein the apparatus is rotatable around the common vertical axis after the first line is formed, then, upon rotation, the at least two support holes are positioned to secure the removable insertion of the marker, to create second points that form a second line, and
      wherein the first line intersects with the second line, and the intersection of the first line and the second line marks the location.

2. The apparatus of claim 1 wherein the horizontal axis of the support device, where the centers of the at least two support holes are placed, coincides with a short axis of the nosepiece of the ultrasound imaging transducer.

3. The apparatus of claim 1 wherein the horizontal axis of the support device where the at least two support holes are placed coincides with a long axis of the nosepiece of the ultrasound imaging transducer.

4. The apparatus of claim 1 wherein the support device comprises at least one clip in proximity of the proximal surface of the support device, and the nosepiece of the ultrasound imaging transducer has at least one corresponding slot for receiving the at least one clip when the support device is installed on the ultrasound imaging transducer.

5. The apparatus of claim 1 wherein the support device comprises at least one of a protrusion or a divot on the proximal surface, and the nosepiece of the ultrasound imaging transducer comprises at least one of a corresponding divot or a corresponding protrusion for mating to the at least one of the protrusion or the divot on the proximal surface when the support device is installed on the ultrasound imaging transducer.

6. The apparatus of claim 1 wherein the proximal surface of the support device matches the shape of the nosepiece of the ultrasound imaging transducer such that the support device is fitted to the ultrasound imaging transducer during assembly and the support device remains fitted to the ultrasound imaging transducer during operation due to friction.

7. The apparatus of claim 1 wherein the ultrasound imaging transducer comprises a transducer array accessible on the nosepiece, and the support device mates with the nosepiece outside of an area of the nosepiece where the transducer array is accessible.

8. The apparatus of claim 1 wherein the vertical axis of the at least two support holes is parallel to the vertical axis of the ultrasound imaging transducer such that when the marker is inserted, the marker is positioned parallel to the vertical axis of the ultrasound imaging transducer.

9. The apparatus of claim 1 wherein the axis of the at least two support holes is inclined relative to the vertical axis of the ultrasound imaging transducer such that when the marker is inserted, the marker is positioned at an angle from the vertical axis of the ultrasound imaging transducer.

10. The apparatus of claim 1, wherein the ultrasound imaging transducer comprises a transducer array, and the centers of the support holes coincide with a center portion of the transducer array.

11. The apparatus of claim 1 wherein the support device comprises additional support holes placed along another horizontal axis of the support device, wherein each of the additional holes are for insertion of the marker.

12. The apparatus of claim 1 wherein the at least two support holes are disposed at opposing ends of the support device.

13. The apparatus of claim 1 wherein the at least two support holes are disposed at opposing sides of the support device.

14. The apparatus of claim 1 wherein the at least two support holes are disposed at opposing ends of the support device and an additional two support holes are disposed at opposing sides of the support device.

15. A support device for coupling to a nosepiece of an ultrasound imaging transducer, for the purpose of ultrasound guided refilling of a drug delivery pump by marking a location for needle insertion, the support device comprising
    a body having a proximal surface configured to engage the nosepiece of the ultrasound imaging transducer, and at least two support holes which penetrate through the body of the support device,
        wherein the centers of the at least two support holes are positioned along a horizontal axis of the support device,
        wherein the at least two support holes secure the removable insertion of a marker, to create first points that form a first line,
        wherein the support device is rotatable around a vertical axis of the ultrasound imaging transducer after the first line is formed, then, upon rotation, the at least two support holes secure the removable insertion of the marker, to create second points that form a second line.

16. The support device of claim 15, wherein the at least two support holes are placed along an axis that corresponds to a short axis of the nosepiece of the ultrasound imaging transducer.

17. The support device of claim 15, wherein the at least two support holes are placed along an axis that corresponds to a long axis of the nosepiece of the ultrasound imaging transducer.

18. The support device of claim 15, comprising at least one clip in proximity to the proximal surface of the support device, the at least one clip for coupling to the nosepiece of the ultrasound imaging transducer.

19. The support device of claim 15, comprising at least one of a protrusion or a divot on the proximal surface for coupling to the nosepiece of the ultrasound imaging transducer.

20. The support device of claim 15, wherein the proximal surface of the support device matches a shape of the nosepiece of the ultrasound imaging transducer such that when the support device is fitted to the ultrasound imaging transducer during assembly it remains fitted thereto due to friction.

* * * * *